(12) United States Patent
Chan et al.

(10) Patent No.: US 6,306,182 B1
(45) Date of Patent: Oct. 23, 2001

(54) POLYMERIC DYE COMPOUNDS AND COMPOSITIONS AND METHODS FOR COLORING HAIR

(75) Inventors: Alexander C. Chan, Cranbury, NJ (US); Geoffrey Robert Hawkins, Langhorne; Alexander Lukacs, III, Wayne, both of PA (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 09/523,262

(22) Filed: Mar. 10, 2000

Related U.S. Application Data

(60) Provisional application No. 60/173,474, filed on Dec. 29, 1999.

(51) Int. Cl.[7] .............................. A61K 7/13; C09B 67/00; C09B 69/10
(52) U.S. Cl. .......................... 8/426; 8/405; 8/587; 8/647; 424/70.1; 424/70.11; 424/70.122; 424/70.17; 424/70.21; 424/70.22; 424/70.27; 424/70.6; 424/70.9
(58) Field of Search .................................. 424/70.6, 70.1, 424/70.11, 70.122, 70.21, 70.9, 70.17, 70.22, 70.27; 8/426, 405, 587, 647

(56) References Cited

U.S. PATENT DOCUMENTS 4,182,612 * 1/1980 Sokol et al. .
5,104,413 * 4/1992 Ikeda .

* cited by examiner

Primary Examiner—Thurman K. Page
Assistant Examiner—P. E. M. Queeney
(74) Attorney, Agent, or Firm—Julie Blackburn

(57) ABSTRACT

A compound of the formula:

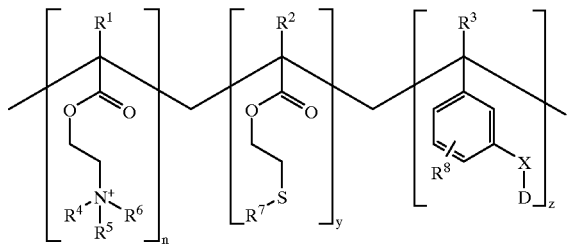

wherein:

n, y, and z are each independently integers ranging from 1 to 100,000;

$R^1$ through $R^6$, and $R^8$ are each independently H, $C_{1-6}$ alkyl, hydroxyalkyl, substituted or unsubstituted aminoalkyl; or $R^4$ and $R^5$ together form a substituted or unsubstituted heterocyclic 5 to 6 membered ring wherein the substituents are selected from $C_{1-6}$ alkyl, hydroxyalkyl, or aminoalkyl;

$R^7$ is H or $SR^1$, or $S$—$R^7$ in the above formula together form an isothiouronium salt or Bunte salt;

X is a linking group; and

D is a chromophore that absorbs visible light; hair dye compositions containing the polymeric compound; and a method for dyeing hair.

20 Claims, No Drawings

POLYMERIC DYE COMPOUNDS AND COMPOSITIONS AND METHODS FOR COLORING HAIR

RELATED APPLICATIONS

This application claims the benefit of U.S. provisional application Ser. No. 60/173,474, filed Dec. 29, 1999.

TECHNICAL FIELD

The invention is in the field of compounds capable of providing color to hair, and the related compositions and methods.

BACKGROUND OF THE INVENTION

A large majority of women color their hair, either to cover gray or change hair color. There are generally three types of hair color: permanent, semi-permanent, and temporary. The term "permanent" generally refers to oxidative dyes, which provide hair color that lasts about four to six weeks. Oxidative hair dyes are usually sold in the form of a two component kit. In one container is an aqueous alkaline composition in the liquid, gel, or creme form that contains oxidative dyes in addition to other ingredients. In the other container is a developer composition that contains an oxidizing agent, usually hydrogen peroxide. The two components are mixed immediately prior to use and applied to hair. The relatively high pH of the composition causes the hair shaft to swell, permitting the dye precursors in the lotion to penetrate the hair shaft. The oxidizing agent then oxidizes the dye precursors, which then combine to form large color molecules within the hair shaft. The mixture is left on the hair for an appropriate period of time, generally 20 to 60 minutes, then rinsed off with water. While consumers who use oxidative dyes appreciate that oxidative dyes provide permanent color, there are certain drawbacks to oxidative dyes that consumers find less than desirable. For example, the peroxide necessary to make the oxidative dye process operable sometimes causes sensitive hair to become dry and brittle. In addition, oxidatively colored hair may undergo further chemical change after two to three weeks, causing the color to fade or exhibit a hue different from the original color. The degree of change varies, with red shades being most susceptible.

Semi-permanent hair color differs in that the dye molecules are preformed prior to application to the hair, and the size of the molecules does not change during the dye process. Semi-permanent dyes will wash out of the hair after about six to twelve shampoos. Semi-permanent hair color is perceived to be gentler to hair because peroxide is not used, as in oxidative hair color.

Temporary hair color is color applied to the hair surface, which is removed with one shampoo. Temporary haircolor is most often used when a unique effect is desired for one day.

Accordingly, the gold standard for haircolor is to provide a composition which does not utilize oxidizing agents such as hydrogen peroxide. The haircolor should provide the same intensity and duration of color as found in oxidative dyes, yet at the same time be gentle and non-drying to the hair.

The object of the invention is to provide a novel class of compounds for use in coloring the hair.

Another object of the invention is to provide a class of polymeric compounds for use in coloring hair, which can be used in hair color systems which are free of oxidizing agents, or contain them in substantially reduced amounts.

Another object of the invention is to provide a method for coloring hair with a haircolor composition containing these polymeric compounds.

SUMMARY OF THE INVENTION

The invention comprises a compound of the formula ("Formula I"):

$$\left[\begin{array}{c} R^1 \\ | \\ \diagup\!\!\!\diagdown \\ O{=}\!\!{=}\!\!O \\ | \\ R^4{-}N^+{-}R^6 \\ | \\ R^5 \end{array}\right]_n \left[\begin{array}{c} R^2 \\ | \\ \diagup\!\!\!\diagdown \\ O{=}\!\!{=}\!\!O \\ | \\ R^7{-}S \end{array}\right]_y \left[\begin{array}{c} R^3 \\ | \\ \diagup\!\!\!\diagdown \\ R^8 \\ \diagdown\!\!\!\diagup\!\!X \\ D \end{array}\right]_z$$

wherein:

n, y, and z are each independently integers ranging from 1 to 100,000;

$R^1$ through $R^6$, and $R^8$ are each independently H, $C_{1-6}$ alkyl, hydroxyalkyl, substituted or unsubstituted aminoalkyl; or $R^4$ and $R^5$ together form a substituted or unsubstituted heterocyclic 5 to 6 membered ring; wherein the substituents are selected from $C_{1-6}$ alkyl, hydroxyalkyl, or aminoalkyl;

$R^7$ is H, $SR^1$; or S—$R^7$ together in the above formula form an isothiouronium salt or Bunte salt;

X is a linking group; and

D is a chromophore that absorbs visible light, and the terminal groups on the polymer may be alkyl, hydroxyl, hydrogen, or substituted alkyl, where the substituents are selected from hydrogen, hydroxyl, halogen, or alkyl.

The invention is further directed to a hair dye composition comprising, by weight of the total composition:

0.01–40% of a polymeric dye compound of Formula I, 0.01–25% of a reducing agent; and 0.1–99% water.

The invention further comprises a method for coloring hair comprising applying an aqueous based hair dye composition containing a polymeric dye compound of Formula I and a reducing agent, to the hair for a period of time sufficient to cause coloration of the hair.

DETAILED DESCRIPTION

The invention comprises a polymeric dye compound capable of causing coloration of hair, a hair dye composition containing the polymeric dye compound, and a method for coloring hair.

I. THE POLYMERIC DYE COMPOUND

The polymeric dye compound of the invention has the following general formula:

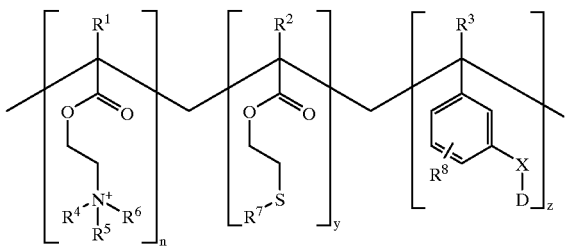

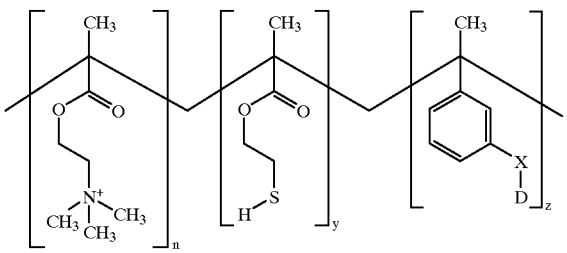

wherein:

n, y, and z are each independently integers ranging from 1 to 100,000;

$R^1$ through $R^6$ and $R^8$ are each independently H, $C_{1-6}$ alkyl, hydroxyalkyl, substituted or unsubstituted aminoalkyl; or $R^4$ and $R^5$ together form a substituted or unsubstituted heterocyclic 5 to 6 membered ring; wherein the substituents are $C_{1-6}$ alkyl, hydroxyalkyl, or aminoalkyl;

$R^7$ is H, $SR^1$, or S—$R^7$ together in the above formula form an isothiouronium salt or Bunte salt;

X is a linking group; and

D is a chromophore that absorbs visible light, and, preferably, the terminal groups on the polymer may be alkyl, hydroxyl, hydrogen, or substituted alkyl, where the substituents are selected from hydrogen, hydroxyl, halogen, or alkyl.

Preferably, in the polymeric dye compound the ratio of n:y:z ranges from 20–70 n units to 30–80 y units, to 1–20 z units. More preferably n, y, and z are each independently integers ranging from 1 to 1,000; most preferably 1 to 100. Where the polymer contains a plurality of any of the three types of units (or mers), it is not required that all of the same type units be strung together as in a block or graft copolymer. The three types of units can be intermingled and can be located anyplace in the polymer chain. It is intended that the above generic formula be so construed.

A variety of linking groups are suitable including the groups —$C_mH_{2m}NR'$—, —NR'—, —NR'C(O)—, —C(O)NR'—, —NR'SO_2$—, —$SO_2NR'$—, —$C_mH_{2m}NR'CO_2$—, or —$C_mH_{2m}CO_2$—, wherein: R' is H, $C_{1-6}$ alkyl, $C_{1-6}$ hydroxyalkyl, or $C_{1-6}$ aminoalkyl; and m is an integer from 0 to 1,000, preferably 1 to 500. As suitable examples of —$C_mH_{2m}NR'$— may be mentioned —$CH_2NH$—, —$C_4H_8NH$—, and —$C_{12}C_{24}NH$—. As suitable examples of —NR'— groups may be mentioned —NH— and $NCH_3$—. As suitable examples of —NR'C(O)— groups may be mentioned $NC_3H_7C(O)$— and $NCH_3C(O)$—. As examples of suitable —C(O)NR'— groups may be mentioned —C(O)$NC_2H_5$— and —C(O)$NC_3H_7$—. As examples of suitable —$NR'SO_2$ groups may be mentioned —$NC_3H_8SO_2$— and —$NC_{12}H_{25}SO_2$. As examples of suitable —$SO_2NR'$— groups are —$SO_2NC_3H_7$— and —$SO_2NC_{12}H_{25}$—. As examples of suitable —$C_mH_{2m}NR'CO_2$— groups may be mentioned —$C_2H_4NCH_3CO$— and —$C_{12}H_{24}NCH_3CO$—. As examples of suitable —$C_mH_{2m}CO_2$— groups may be mentioned —$CH_2CH_2CO_2$— and —$CH_2CH_2CO_2$—.

In the preferred compound, S—$R^7$ together forms an isothiouronium salt; and X is a linking group —$C_mH_{2m}NR'CO_2$— or —$(CH_3)_2CNHCO_2$—. Most preferably $R^1$ through $R^6$, and $R^8$ are methyl; and m=2. Most preferred is a polymeric dye compound of the formula:

wherein X is —$C_mH_{2m}NHCO_2$— and n, y, and z are each independently 1–100.

The chromophore, D, that may be used is any chromophore that is suitable for use in dyeing hair or textile fibers, and which is capable of absorbing visible light, e.g. light in the fluorescent wavelength range. Examples of these chromophores include radicals of monoazo, diazo, polyazo dyes or metallic derivatives thereof. Further examples include anthroquinones, phthalocyanine, formazan, azomethine, dioxazine, phenazine, stilbene, triphenylmethane, xanthene, thioxanthene, nitroaryl, naphthoquinone, pyrenequionone, and the like. Particularly preferred chromophores are monoazo chromophores. The polymeric dye compounds of the invention may be made by free radical initiated addition polymerization of methacrylates and styrenes which may bear the dye chromophores, the pending groups bearing the thio moiety and the aminoalkyl. The chromophore can be attached to the polymer after the various monomers have been polymerized, or, if desired, it may be attached to the monomer prior to polymerization. In the case where the dye is attached to the monomer prior to polymerization, this may be accomplished by reacting the dye with halogen substituted monomer, e.g. methacrylol chloride.

II. HAIR DYE COMPOSITION

The invention comprises a hair dye composition comprising comprising, by weight of the total composition:

0.01–40% of a polymeric dye compound of Formula I,
0.01–25% of a reducing agent; and
0.1–99% water.

A. Polymeric Dye Compound

The polymeric dye compound used in the compositions is of Formula I, above. Preferably, the compositions contain 0.1–35%, more preferably 0.5–20% by weight of the total composition of the polymeric dye compound of Formula I.

B. Reducing Agent

The dye composition comprises 0.01–25%, preferably 0.1–20%, more preferably 0.5–15% by weight of the total composition of a reducing agent. The term "reducing agent" means a compound capable of accepting electrons from a disulfide functional group on any compound or molecule. Suitable reducing agents are those compounds typically used in permanent waving of hair, including thio compounds such as bisulfites, ammonium thioglycolate, glyceryl monothioglycolate, ammonium thiolactate, benzoisothiazolinone, bispyrithione, butyl thioglycolate, calcium sulfide, calcium thioglycolate, cysteamine, cysteamine hydrochloride, acetyl cysteine, cysteine, cysteine hydrochloride, diammonium thioglycolate, methionine, phenylthioglycolic acid, potassium thioglycolate, sodium thioglycolate, and those thio compounds set forth on pages 1603 and 1604 of the CTFA Cosmetic Ingredient Dictionary and Handbook, Second Edition, 1997, which is hereby incorporated by reference.

C. Water

The hair dye compositions of the invention are aqueous based and contain about 1–99%, preferably 2–90%, more preferably 5–85% by weight of the total composition of water. The composition may be found in a variety of pH ranges, from 4 to 10. More preferably, the pH is in the neutral range.

D. Other Ingredients

The hair dye compositions of the invention may contain one or more additional ingredients to improve the aesthetic properties of the compositions, such as thickening agents, humectants, surfactants, UV absorbers, conditioning agents, preservatives, pH adjusters, anti-oxidants, fragrances, and the like.

1. Humectants

A variety of humectants are suitable, and suggested ranges are 0.1–35%, preferably 0.5–30%, more preferably 1–25% by weight of the total composition. Suitable humectants include glycerin, urea, polyethylene glycols, sugars such as glucose, fructose, and so on. Preferably, the humectant is urea.

2. Surfactants

The hair dye compositions may additionally contain one or more surfactants, such as anionic, nonionic, cationic, zwitterionic, or amphoteric surfactants. Suitable surfactants are those set forth in U.S. Pat. No. 5,843,193, which is hereby incorporated by reference in its entirety.

3. Conditioning Agents

It may also be desirable to including one or more conditioning agents in the hair dye compositions. Suggested ranges are 0.01–20%, preferably 0.05–15%, more preferably 0.1–10% by weight of the total composition. Examples of conditioning agents include various silicone and organic oils that are liquids at room temperature. The silicone oils may be volatile or nonvolatile, and include cyclomethicone, dimethicone, dimethicone copolyol, amodimethicone, trimethylsilylamodimethicone, and the like. Various organic oils include fatty oils as described in U.S. Pat. No. 5,843,193, and paraffinic hydrocarbons such as mineral oil, C20-40 isoparaffins, and so on.

III. THE METHOD

The invention further comprises a method for coloring hair comprising applying an aqueous based hair dye composition containing a polymeric dye compound of Formula I and a reducing agent, to the hair for a period of time sufficient to cause coloration of the hair. The composition is applied to the hair and allowed to remain on the hair for about 5 to 50 minutes, depending on the type and texture of the user's hair. The hair is then rinsed well with water to remove the composition. If desired, a hair conditioner may be applied to the hair for 30 second to 5 minutes, to further condition the hair. However, since the compositions of the invention are very gentle to hair, it is not necessary to further condition the hair.

The hair dye compositions may be sold in a one container package, where it is not necessary for the consumer to mix two compositions together immediately prior to use. This is substantially more convenient and economical than the conventional two component kits which require mixing of two separate compositions immediately prior to use. This mixture must be used immediately otherwise it becomes inactive.

The invention will be further described in connection with the following examples which are set forth for the purposes of illustration only.

EXAMPLE 1

A polymer for use in coloring hair was made by combining 30.7 grams of 2-(N,N-dimethylaminoethyl) methacrylate; 50.0 grams of isothiouronium methacrylate; 10.9 grams of a monomer made by polymerizing Disperse Red 58 with methacryloyl choride in dry dichloromethane in the presence of triethylamine; 1.38 grams 2,2-azo-bis(2-methylpropionamidine)dihydrochloride (catalyst) in 92.0 grams of ethanol. The mixture was stirred in a flask maintained at 70° C. under a postive nitrogen atmosphere. The reaction was monitored by Raman spectroscopy until the peak at 1636 cm$^{-1}$ was no longer detected (an indication that the monomers have polymerized), after which the mixture thickened significantly. At the end of the reaction, water was added so that the final concentration of solids was about 35% by weight. After evaporation of the solvent, the resulting polymer was a dark red solid of Formula I, where $R^1$ through $R^5$ were methyl, $R^6$ and $R^8$ are H, and S—$R^7$ together form an isothiouronium salt, X is —$(CH_3)_2CNHCO_2$—, said polymer having the general formula:

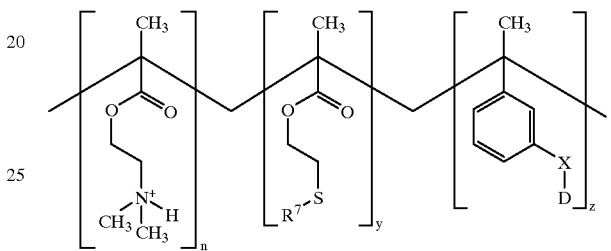

wherein D is:

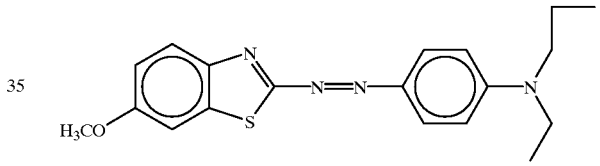

and n, y, and z are each independently 1 to 100.

EXAMPLE 2

Without isolation, the polymer from Example 1 was reacted with 24.83 grams of dimethyl sulfate. The temperature was maintained at 40° C. with stirring for four hours. This caused the polymer to quaternize, forming a dark blue violet material that produced a film after the solvent was evaporated. Resulting polymer had the same formula as the polymer of Example 1, except that D was:

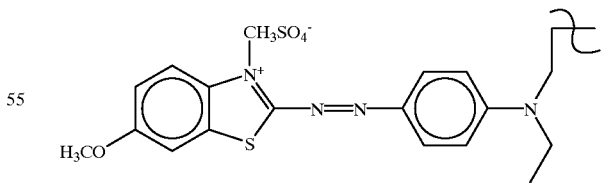

EXAMPLE 3

Without isolation, the pH of the reaction product of Example 2 was adjusted to 9.5 to 10 by adding a sufficient amount of a 10% aqueous solution of sodium hydroxide, and the final mixture was stirred, causing the isothiouronium group on the polymer to react with the sodium hydroxide to form a mercaptan. The resulting polymer had the structure of the polymer in Example 2, except that R7 was H, the polymer having the general formula:

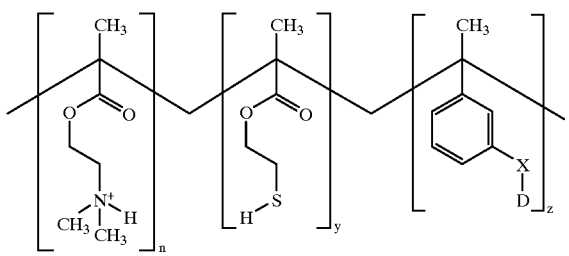

and wherein X and D are as described in Example 2 and the ratio of n:y:z was 10:9:1 respectively.

EXAMPLE 4

A composition for dyeing hair was prepared as follows:

|  | w/w % |
| --- | --- |
| Glyceryl monothioglycolate | 4.00 |
| Urea (humectant and swelling agent for hair) | 10.00 |
| Polymer* | 8.40 |
| Ethanol | 8.43 |
| Water QS to 100 | |
| Acetic acid QS to pH 7.0 | |

*The polymer had the following structure:

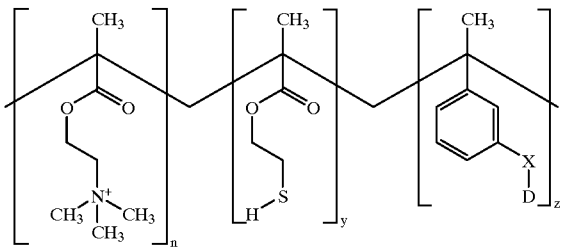

wherein n:y:z was 10:9:1 respectively, and X and D are as defined in Example 2.

The composition was applied to gray hair for twenty to thirty minutes and provided suitable deep blue color to the hair.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:
1. A compound of the formula:

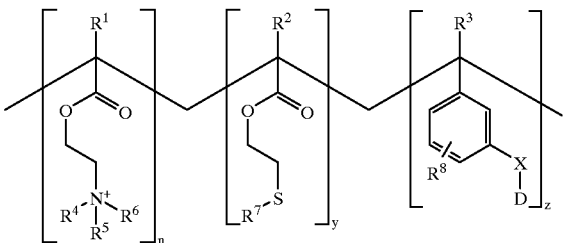

wherein:
n, y, and z are each independently integers ranging from 1 to 100,000;
$R^1$ through $R^6$ and $R^8$ are each independently H, $C_{1-6}$ alkyl, hydroxyalkyl, substituted or unsubstituted aminoalkyl; or $R^4$ and $R^5$ together form a substituted or unsubstituted heterocyclic 5 to 6 membered ring wherein the substituents are selected from $C_{1-6}$ alkyl, hydroxyalkyl, or substituted or unsubstituted aminoalkyl;
$R^7$ is H, $SR^1$, or S and $R^7$ together form an isothiouronium salt or Bunte salt;
X is a linking group; and
D is a chromophore that absorbs visible light.
2. The compound of claim 1 wherein the ratio of n:y:z ranges from 20–70 to 30–80 to 1–20 respectively.
3. The compound of claim 1 wherein n, y, and z are each independently integers ranging from 1 to 1,000.
4. The compound of claim 3 wherein n, y, and z are each independently integers ranging from 1 to 100.
5. The compound of claim 1 wherein S—$R^7$ together form an isothiouronium salt.
6. The compound of claim 1 wherein X is a linking group selected from the group consisting of:

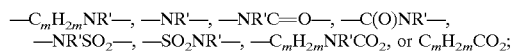

wherein:
R' is H, $C_{1-6}$ alkyl, $C_{1-6}$ hydroxyalkyl, or aminoalkyl; and
m is an integer from 0 to 1,000.
7. The compound of claim 6 wherein m is 1–100.
8. The compound of claim 1 wherein $R^1$, $R^2$, and $R^3$ are each independently $C_{1-6}$ alkyl.
9. The compound of claim 8 wherein $R^1$, $R^2$, and $R^3$ are methyl.
10. The compound of claim 1 wherein $R^7$ is H.
11. The compound of claim 6 wherein the linking group $R^1$ is H and the linking group is —(CH$_3$)$_2$CNHCO$_2$—.
12. A hair dye composition comprising, by weight of the total composition:
0.01–40% of a polymeric dye compound of Formula I,
0.01–25% of a reducing agent; and
0.1–99% water.
13. The composition of claim 12 wherein the reducing agent is a thio compound.
14. The composition of claim 13 wherein the reducing agent is a thioglycolate.
15. The composition of claim 14 wherein the thioglycolate is glyceryl thioglycolate.
16. The composition of claim 12 further comprising a humectant selected from the group consisting of glycol, urea, sugar, and polyethylene glycol.

17. The composition of claim 16 wherein the humectant is urea.

18. A method for coloring hair comprising applying an aqueous based hair dye composition containing a polymeric dye compound of Formula I and a reducing agent, to the hair for a period of time sufficient to cause coloration of the hair.

19. The method of claim 18 where the composition is applied to hair for 5 to 50 minutes.

20. The method of claim 19 wherein the composition is removed from the hair by rinsing with water.

* * * * *